(12) United States Patent
Chiba

(10) Patent No.: US 11,613,734 B2
(45) Date of Patent: Mar. 28, 2023

(54) METHOD OF COLLECTING FOR EXOSOME

(71) Applicant: FULLSTEM CO., LTD., Okinawa (JP)

(72) Inventor: Shunmei Chiba, Okinawa (JP)

(73) Assignee: FULLSTEM CO., LTD., Okinawa (JP)

( * ) Notice: Subject to any disclaimer, the term of this patent is extended or adjusted under 35 U.S.C. 154(b) by 0 days.

(21) Appl. No.: 17/619,128

(22) PCT Filed: Jun. 11, 2021

(86) PCT No.: PCT/JP2021/022313
§ 371 (c)(1),
(2) Date: Jul. 19, 2022

(87) PCT Pub. No.: WO2022/259525
PCT Pub. Date: Dec. 15, 2022

(65) Prior Publication Data
US 2022/0396771 A1    Dec. 15, 2022

(51) Int. Cl.
*C12N 5/0775* (2010.01)

(52) U.S. Cl.
CPC ......... *C12N 5/0667* (2013.01); *C12N 5/0663* (2013.01); *C12N 2500/34* (2013.01); *C12N 2513/00* (2013.01); *C12N 2533/00* (2013.01)

(58) Field of Classification Search
None
See application file for complete search history.

(56) References Cited

U.S. PATENT DOCUMENTS

| | | | |
|---|---|---|---|
| 2019/0137338 A1 | 5/2019 | Webster et al. | |
| 2020/0040304 A1* | 2/2020 | Kanaki | A61L 27/38 |
| 2021/0052641 A1* | 2/2021 | Tiet | A61K 35/12 |
| 2021/0155887 A1 | 5/2021 | Chiba et al. | |
| 2021/0207084 A1 | 7/2021 | Chiba | |

FOREIGN PATENT DOCUMENTS

| | | |
|---|---|---|
| CN | 112410292 A | 2/2021 |
| EP | 3647407 A1 | 5/2020 |
| EP | 32492578 B1 | 5/2021 |
| JP | 2019-156786 A | 9/2019 |
| WO | WO-2013/150303 A1 | 10/2013 |
| WO | WO-2018/123966 A1 | 7/2018 |
| WO | WO 2018/182356 A1 | 10/2018 |
| WO | WO-2019/071076 A1 | 4/2019 |
| WO | WO 2019/099927 A1 | 5/2019 |
| WO | WO-2019/160000 A1 | 8/2019 |
| WO | WO 2020/261257 | 12/2020 |

OTHER PUBLICATIONS

Nuschke et al. "Mesenchymal stem cells/multipotent stromal cells (MSCs) are glycolytic and thus glucose is a limiting factor of in vitro models of MSC starvation" (2016) Stem Cell Res Ther 7:179 pp. 1-9 (Year: 2016).*

Chamberlain et al., *Concise Review: Mesenchymal Stem Cells: Their Phenotype, Differentiation Capacity, Immunological Features, and Potential for Homing*, Stem Cells 25 (2007) 2739-2749.

Simmons et al., *vesicular carriers for intercellular communication*, Science Direct, Current Opinion in Cell Biology, 2009, 21:575-581.

Skog et al., *Glioblastoma microvesicles transport RNA and protein that promote tumor growth and provide diagnostic biomarkers*, Nat Cell Biology Dec. 2008, 10:1470-1476.

Valadiet al., *Exosome-mediated transfer of mRNAs and microRNAs is a novel mechanism of genetic exchange between cells*, Nat Cell Biology 2007, 9:654-659.

Katsuda et al., *The therapeutic potential of mesenchymal stem cell-derived extracellular vesicles*, Proteomics 2013, 13, 1637-1653.

Chen et al., *Microfluidic isolation and trans criptome analysis of serum microvesicles*, Lab Chip. Feb. 21, 2010; 10(4):505-511.

Cao et al., *Three-dimensional culture of MSCs produces exosomes with improved yield and enhanced therapeutic efficacy for cisplatin-induced acute kidney injury*, Stem Cell Research & Therapy, vol. 11 (206), pp. 1-13 (2020).

English translation of the International Search Report for PCT/JP2021/022313 (ISA/JP) dated Aug. 16, 2021 (3 pages).

* cited by examiner

*Primary Examiner* — Teresa E Knight
(74) *Attorney, Agent, or Firm* — Alston & Bird LLP

(57) ABSTRACT

A method of efficiently recovering a large amount of exosomes from mesenchymal stem cells is provided. The method includes: a three dimensional culture step of three dimensionally culturing mesenchymal stem cells in a medium containing sugar by using a nonwoven fabric as a scaffold; a post-plateau culture step of further culturing for a certain period of time after the amount of the sugar consumed by the mesenchymal stem cells reaches a plateau; and an exosome recovery step of recovering exosomes from the mesenchymal stem cells. The mesenchymal stem cells are adipose-derived mesenchymal stem cells.

8 Claims, 2 Drawing Sheets

METHOD OF COLLECTING FOR EXOSOME

CROSS REFERENCE TO RELATED APPLICATIONS

This application is a national stage application, filed under 35 U.S.C. § 371, of International Application No. PCT/JP2021/022313, filed Jun. 11, 2021, the contents of which as are hereby incorporated by reference in their entirety.

BACKGROUND

Technical Field

The present invention relates to a method of recovering exosomes from mesenchymal stem cells.

Description of Related Art

Mesenchymal stem cells (MSCs) are multipotent stem cells present in mesenchymal tissues, i.e., mesoderm-derived connective tissues. It has also been revealed that undifferentiated mesenchymal stem cells secrete cytokines and growth factors having an anti-inflammatory effect, a cell-growth-promoting effect, an angiogenesis-promoting effect, and the like, and support tissue repair via paracrine (Non-Patent Document 1). A molecular group secreted by the undifferentiated mesenchymal stem cells has therapeutic effects on various diseases not limited to a specific disease. Tissue regeneration becomes possible by using naive mesenchymal stem cells without inducing differentiation of the mesenchymal stem cells into cells of a tissue to be repaired and without adding any artificial operation such as gene recombination to the cells.

Exosomes can mediate intercellular communication by transferring proteins, lipids and RNA between cells (Non-Patent Documents 2 and 3). It has been revealed that molecules such as those of proteins, microRNAs, and mRNAs contained in exosomes have functions similar to those of cells from which the exosomes are derived. Therefore, exosomes secreted by mesenchymal stem cells, which have attracted attention as a source of cell therapy for a wide range of diseases, are expected to have the same therapeutic effect as MSCs (Non-Patent Document 4).

Patent Document 1 describes exosomes isolated from a cultured neural stem cell line (NSCL). The exosomes can promote migration of fibroblasts, branching of human umbilical vein endothelial cells, and extension of neurites.

Exosomes contain relatively less animal serum than stem cells, and can eliminate the risk of symptoms due to animal serum infection. Therefore, cell therapy using exosomes can overcome the limitations of existing stem cell therapies.

A technique for recovering exosomes includes an ultracentrifugation technique and a precipitation technique, but it is difficult to recover a large amount of exosomes required for the therapy by these techniques. Patent Document 2 discloses an exosome recovery method using a sphingoid base. However, the exosome recovery method described in Patent Document 2 is limited to recovery of exosomes in nerve cells in order to cure Alzheimer's disease.

Non-Patent Document 5 discloses a technique of producing a device where anti-CD63 antibodies are immobilized and using a microfluidic system of isolating and recovering vesicles from several hundred μl of serum sample. However, the exosome recovery method described in Non-Patent Document 5 is still insufficient in yield because the method is achieved by capturing antibodies, and it is necessary to construct a technique for recovering a large amount of exosomes.

CITATION LIST

Patent Document 1: WO 2013/150303
Patent Document 2: Japanese Unexamined Patent Publication No. 2019-156786
Non-Patent Document 1: Chamberlain G, Fox J, Ashton B, Middleton J, Concise review. mesenchymal stem cells: their phenotype, differentiation capacity, immunological features, and potential for homing. Stem Cells. 25 (2007) 2739-2749
Non-Patent Document 2: Simons and Raposo, Curropin Cell Biology 2009; 21:575-581
Non-Patent Document 3: Skog et al., Nat Cell Biology 2008; 10:1470-1476; Valadi et al., Nat Cell Biology 2007; 9:654-659
Non-Patent Document 4: Katsuda T, Kosaka N, Takeshita F, Ochiya T. The therapeutic potential of mesenchymal stem cell-derived extracellular vesicles. Proteomics. 13 (2013) 1637-1653
Non-Patent Document 5: Chen, C., Skog, J., Hsu, C., Lessard, R. T., Balaj, L., Wurdinger, T., Carter, B. S., Breakefield, X. O., Toner, M., Irimia, D. Microfluidic isolation and transcriptome analysis of serum microvesicles. Lab Chip. 10, 505-511(2010)

BRIEF SUMMARY

The present invention has been made in view of such problems, and an object thereof is to provide an exosome recovery method of recovering a larger amount of exosomes from mesenchymal stem cells.

The exosome recovery method of the present invention is directed to a method of recovering exosomes from mesenchymal stem cells. The method includes: a three dimensional culture step of three dimensionally culturing mesenchymal stem cells in a medium by using a nonwoven fabric as a scaffold while measuring an amount of substance metabolized by the mesenchymal stem cells which is in the medium; a post-plateau culture step of further culturing for a certain period of time after the amount of the substance in the medium reaches a plateau; and an exosome recovery step of recovering exosomes from the mesenchymal stem cells after the culturing for the certain period of time. Exosomes are membrane vesicles released from cells to the outside of the cells. Exosomes include miRNAs, mRNAs, lncRNAs, proteins, small metabolic molecule compounds, and the like derived from cells that have released exosomes into lipid bilayer membrane envelopes.

According to the present invention, it is possible to efficiently recover a large amount of exosomes from mesenchymal stem cells.

DETAILED DESCRIPTION OF VARIOUS EMBODIMENTS

Figure 1:
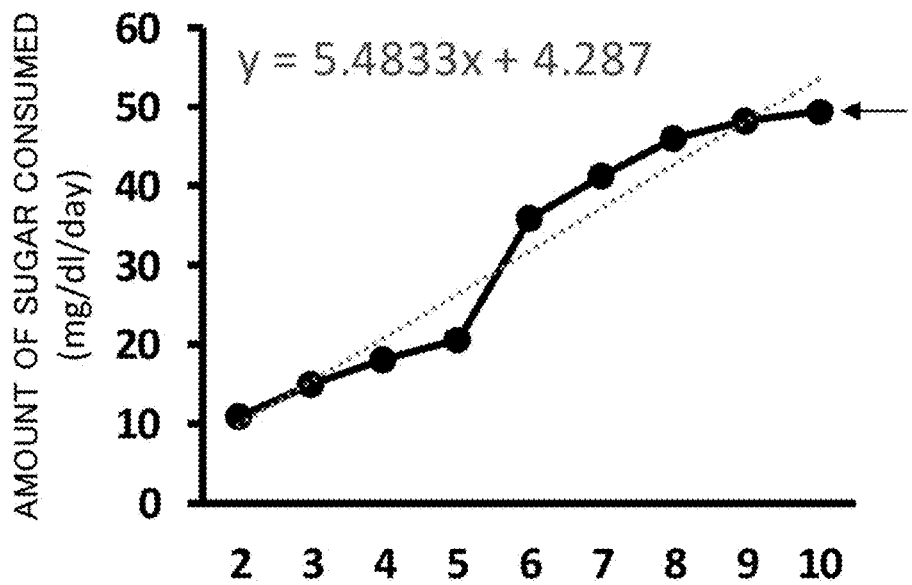
FIG. 1 is a graph showing a relationship between the amount of sugar consumed and a culture time in culturing of bone marrow-derived mesenchymal stem cells by using a nonwoven fabric as a scaffold.

Embodiments of the present invention will be described in detail below while referring to the accompanying drawings. The embodiments are only intended to facilitate the understanding of the principles of the present invention and the scope of the present invention is not limited to the following embodiments. Other embodiments where a person skilled in the art can appropriately replace configurations of the embodiments below are included within the scope of the present invention.

The exosome recovery method of the present invention includes: (1) a three dimensional culture step of three dimensionally culturing mesenchymal stem cells in a medium by using a nonwoven fabric as a scaffold while measuring an amount of substance metabolized by the mesenchymal stem cells which is in the medium; (2) a post-plateau culture step of further culturing for a certain period of time after the amount of the substance in the medium reaches a plateau; and (3) an exosome recovery step of recovering exosomes from the mesenchymal stem cells after the culturing for the certain period of time. The present inventors have newly found that further culturing for a certain period of time after the amount of substance in the medium consumed by the cells due to metabolization of the cells or the amount of substance yielded from the cells in the medium reaches a plateau in addition to culturing of mesenchymal stem cells by using a nonwoven fabric as a scaffold significantly increases the amount of exosomes recovered from the mesenchymal stem cells, and completed the present invention based on the finding.

(1) Three Dimensional Culture Step

In the three dimensional culture step, mesenchymal stem cells are three dimensionally cultured in a medium by using a nonwoven fabric as a scaffold while measuring an amount of substance metabolized by the mesenchymal stem cells which is in the medium ("three dimensional" and "three dimensionally" herein may also be referred to as "3D).

The mesenchymal stem cells from which exosomes are yielded are cells belonging to the mesenchymal system, and mean cells that have an ability to differentiate into one or more types of cells (such as osteocytes, cardiomyocytes, chondrocytes, tenocytes, and adipocytes), preferably two or more types of cells, more preferably three or more types of cells, and can proliferate while maintaining the ability. Examples of the tissue containing mesenchymal stem cells include adipose tissue, umbilical cord, bone marrow, umbilical cord blood, endometrium, placenta, amnion, chorion, decidua, dermis, skeletal muscle, periosteum, dental follicle, periodontal ligament, dental pulp, and dental embryo. Specifically, the mesenchymal stem cells can be adipose-derived mesenchymal stem cells (also referred to as ADSCs), bone marrow-derived mesenchymal stem cells (also referred to as BMSCs), umbilical cord-derived mesenchymal stem cells, placenta-derived mesenchymal stem cells, dental pulp-derived mesenchymal stem cells, or the like, preferably adipose-derived mesenchymal stem cells or bone marrow-derived mesenchymal stem cells, particularly preferably adipose-derived mesenchymal stem cells.

Adipose-derived mesenchymal stem cells have advantageous features such as rapid cell proliferation, increased secretion of regeneration promoting factors, and high immunosuppressive ability, as compared with bone marrow-derived mesenchymal stem cells. In addition, adipose-derived mesenchymal stem cells obtained from adipose tissue of the abdomen or buttocks can be easily obtained in a sufficient amount in a safe manner, which is also an advantageous feature, as compared with bone marrow-derived mesenchymal stem cells for which bone marrow needs to be collected. In addition, the use of mesenchymal stem cells derived from autologous adipose tissue of a subject for treatment of the subject is excellent in having no ethical problem, no immune rejection, few problems such as infection, and a therapeutic effect when administered intravenously.

The medium is a medium for mesenchymal stem cells, and examples thereof include DMEM, MEMα, DMEM/F12, and MEM. The substance in a medium, metabolized by the mesenchymal stem cells, is not particularly limited, and examples thereof include sugars. The substance is preferably glucose among the sugars. The substance yielded in the medium by metabolization of the mesenchymal stem cells is not particularly limited, and examples thereof include LDH and lactic acid.

The scaffold used is a nonwoven fabric. The mass of the nonwoven fabric per unit area may be 1 g/m$^2$ to 500 g/m$^2$, and is, for example, preferably 50 g/m$^2$ to 200 g/m$^2$. The nonwoven fabric may be a hydrophilized nonwoven fabric. The nonwoven fabric can be hydrophilized by a fluorine gas treatment, an atmospheric pressure plasma treatment, a vacuum plasma treatment, a corona treatment, a graft polymerization treatment of a hydrophilic monomer, a sulfonation treatment, or a surfactant application treatment, and preferably by the fluorine gas treatment or the atmospheric pressure plasma treatment.

Fibers constituting the nonwoven fabric are preferably a polyolefin-based polymer, and examples of the polyolefin-based polymer include polymers of ethylene, propylene, 1-butene, 1-pentene, 3-methyl-1-butene, 1-hexene, 1-octene, 1-dodecene, and 1-octadecene.

The fibers constituting the nonwoven fabric are preferably fibers having a small fiber diameter, and the average fiber diameter is preferably 200 μm or less, more preferably 010 μm to 100 μm, particularly preferably 15 μm to 50 μm. The fibers may be a mixture of fibers having a relatively large fiber diameter and fibers having a relatively small fiber diameter.

The nonwoven fabric woven fabric is preferably porous. Porosity is important to supply sufficient amounts of oxygen and nutrients to cells for tissue regeneration, and to quickly remove carbon dioxide and waste products. In addition, the nonwoven fabric having porosity has a larger specific surface area and enhances cell adhesion. The average pore diameter in such a case is, for example, 5 μm to 200 μm, 20 μm to 100 μm, 25 μm to 100 μm, 30 μm to 100 μm, 35 μm to 100 μm, 40 μm to 100 μm, 50 μm to 100 μm, or 60 μm to 100 μm, preferably 50 μm to 300 μm.

The form of the nonwoven fabric is not particularly limited, and is preferably a nonwoven fabric sheet. The nonwoven fabric sheet preferably has a plurality of through holes penetrating in the thickness direction. The total film thickness of the nonwoven fabric sheet may be, for example, 5 μm or more, 10 μm or more, 20 μm or more, or 25 μm or more, and may be 500 μm or less, 300 μm or less, 100 μm or less, 75 μm or less, or 50 μm or less. The total film thickness is preferably 30 μm to 2000 μm, more preferably 500 μm to 1000 μm.

In the three dimensional culture step, mesenchymal stem cells are three dimensionally cultured while measuring the amount of substance in a medium, metabolized by the mesenchymal stem cells, and the culturing is continued until the amount of this substance in the medium reaches a plateau. In culturing of cells by using a culture dish as a scaffold, cells proliferate two dimensionally. It is thus easy to observe the state where the surface of the culture dish is covered with the cells. However, in culturing of cells by using a nonwoven fabric as a scaffold, cells proliferate three dimensionally. It is thus difficult to observe the state where the nonwoven fabric is covered with the cells. Therefore, the culturing is continued until the amount of the substance in a medium, consumed or yielded by the cells, reaches a plateau.

The measurement of the amount of the substance in a medium, consumed or yielded by the cells, is not particularly limited, but for the measurement of the amount of the substance in the medium, consumed by the cells, the amount of sugar consumed by the mesenchymal stem cells is measured for each culture time, for example. Preferably, the amount of glucose in the medium is measured as described above. For the measurement of the amount of glucose consumed by the mesenchymal stem cells, a commercially available glucose assay kit for measuring the amount of glucose in a cell culture supernatant can be used, in which the measurement can be performed by reacting an enzyme with 2-deoxyglucose which has been taken into the cells.

Determination that the amount of the substance in the medium, consumed or yielded by the cells, reaches a plateau is not particularly limited, and for example, a graph of the amount of the substance in the medium versus the number of days of the culturing is prepared, and a linear function ($y=ax+b$) as an approximate line is derived from the graph, and a point at which the slope a of the liner function becomes flat is determined as a point at which the amount of the substance reaches a plateau. At the point at which the slope a of the linear function as an approximate line becomes flat, $-0.1 \leq a \leq 0.1$, preferably $-0.01 \leq a \leq 0.01$, more preferably $a=0$, for example. Determination of the point at which the amount of the substance reaches a plateau may be made based on not only the point at which the slope a of the linear function ($y=ax+b$), which is an approximate line for relational equation between the amount of the substance in the medium versus the number of days of the culturing, becomes flat, but also the point at which the amount of the substance consumed or yielded in the medium becomes minus. At the point at which the slope a of the linear function as an approximate line becomes minus, $-0.5 \leq a \leq -0.01$, preferably $-0.1 \leq a \leq -0.05$, for example.

(2) Post-Plateau Culture Step

In the post-plateau culture step, culturing is further performed for a certain period of time after the amount of the substance in the medium, consumed or yielded by the mesenchymal stem cells, reaches a plateau.

A culture time after the amount of the substance in the medium reaches a plateau is not particularly limited, and is, for example, 12 hours to 72 hours, preferably 18 hours to 66 hours, more preferably 24 hours to 60 hours, particularly preferably 36 hours to 54 hours, most preferably 48 hours.

(3) Exosome Recovery Step

Finally, exosomes are recovered from the mesenchymal stem cells. After the completion of the post-plateau culture step, a larger amount of exosomes is yielded, and the exosomes can be recovered by a commonly used technique. Although not particularly limited thereto, the technique for recovering exosomes includes, for example, an ultracentrifugation technique. Examples of the ultracentrifugation technique include a pelleting down technique, a sucrose cushion technique, and a density gradient centrifugation technique.

The exosomes obtained using the exosome recovery method according to the present invention can be used as an exosome-containing formulation. Although not particularly limited thereto, examples of the form of the exosome-containing formulation includes: liquids such as an injection, a suspension, a solution, and a spray; a sheet-like formulation; and a gel-like formulation.

The exosome-containing formulation can be used without limitations, and can be used, for example, for direct administration into a subject, or as a source for reconstruction of tissues and organs in vitro.

The exosome-containing formulation can be used to treat diseases and disorders. Examples of the target diseases and disorders include inflammatory bowel disease including immunologic disease, ischemic disease (such as lower limb ischemia and ischemic heart disease (such as myocardial infarction), coronary heart disease, cerebrovascular ischemia, renal ischemia, and pulmonary ischemia), neurological disease, Crohn's disease, graft-versus-host disease (GVHD), and ulcerative colitis; connective tissue diseases such as systemic lupus erythematosus; hepatic cirrhosis, cerebral infarction, intracerebral hematoma, cerebral vasospasm, radiation enteritis, atopic dermatitis, multiple sclerosis, rheumatoid arthritis, psoriasis, lupus erythematosus, diabetes, mycosis fungoides, (Alibert-Bazin syndrome), scleroderma, diseases caused by degeneration and/or inflammation of connective tissues such as bones, eye disease, angiogenesis related disease, congestive heart failure, cardiomyopathy, wound, epithelial damage, fibrosis, pulmonary disease, and cancer.

The exosome-containing formulation may also be used for treatment, care, or improvement for cosmetic purposes. Cosmetic purposes are not only purely for the purpose of beauty in the healthy state, but also for treatments for post-surgical or post-traumatic deformities and congenital deformities. For example, the exosome-containing formulation can be used for breast tissue augmentation (breast augmentation, breast reconstruction), tissue augmentation of cheek or upper and lower eyelid depressions, and tissue augmentation for facial hemiatrophy and of face or funnel chest.

The exosome-containing formulation may contain a pharmaceutically acceptable carrier or additive besides exosomes. Although not particularly limited thereto, examples of such carrier and additive include a tonicity agent, a thickener, saccharides, sugar alcohols, an antiseptic (preservative), a fungicide or antibiotic, a pH adjusting agent, a stabilizing agent, a chelating agent, an oleaginous base, a gel base, a surfactant, a suspending agent, a binder, a filler, a lubricant, a disintegrant, a foaming agent, a glidant, a dispersant, an emulsifier, a buffer, a solubilizer, an antioxidant, a sweetening agent, an acidulant, a colorant, a taste making agent, a flavor, and a cooling agent.

EXAMPLES

1. Recovery of Large Amount of Exosomes by Use of Nonwoven Fabric (3D) as Scaffold (Examples)

Examples of recovering a large amount of exosomes after culturing by the use of a nonwoven fabric (3D) as a scaffold and further culturing with the amount of sugar consumed being plateau will be described below.

1-1. Three Dimensional Culture Step

In the three dimensional culture step, cells were three-dimensionally cultured by using a nonwoven fabric as a scaffold until the amount of sugar consumed by the cells (in this example, the amount of glucose in a medium) reached plateau.

Bone marrow-derived mesenchymal stem cells (BMSCs) and adipose-derived mesenchymal stem cells (ADSCs) were seeded on the scaffold. The scaffold used was a nonwoven fabric (3D, BioNOCII, manufactured by CESCO, in a non-adherent 24 well plate (PrimeSurface (registered trademark) manufactured by Sumitomo Bakelite Co., Ltd.) having a three-dimensional structure.

To each of the wells, $6 \times 10^3$ cells were seeded for BMSCs, and $4 \times 10^4$ cells were seeded for ADSCs. A basal medium was 1.5 ml of 10% FBS/DMEM F12 (Sigma-Aldrich). DMEM/F12 is a medium obtained by mixing DMEM (including glucose) and Ham's F-12 at 1:1, and 10% FBS was added to the DMEM/F12.

Starting from Day 2, 1.5 ml of medium was exchanged daily, and the amount of sugar consumed in the used culture medium was measured. The culturing was continued until the amount of sugar consumed by the cells reached a plateau. The culture time until the amount of sugar consumed reached a plateau was 10 days for BMSCs. The culture time until the amount of sugar consumed reached a plateau was 8 days for ADSCs.

1-2. Post-Plateau Culture Step

In the post-plateau culture step, the cells were three-dimensionally cultured for a certain period of time after the amount of sugar consumed by the cells reached plateau.

Specifically, the medium was exchanged immediately after the amount of sugar consumed by BMSCs and ADSCs began to a plateau. A medium used was the one obtained by adding 10% ExoFBS (Funakoshi Co., Ltd.) to DMEM F12. BMSCs and ADSCs were cultured for 48 hours after the exchange of the medium. Specifically, for BMSCs, the amount of sugar consumed reached a plateau after 10 days of the culturing. The medium was then exchanged for DMEM F12+10% ExoFBS, and the further culturing was performed for 48 hours. For ADSCs, the amount of sugar consumed reached a plateau after 8 days of the culturing. The medium was then exchanged for DMEM F12+10% ExoFBS, and the further culturing was performed for 48 hours.

1-3. Exosome Recovery Step

The total of 1.5 ml of conditioned medium was collected after the culturing of BMSCs and ADSCs for 48 hours. Exosomes were then recovered from the collected conditioned medium by using the ultracentrifugation technique. The cells were also detached from the scaffold, and the final cell count was measured.

2. Recovery of Exosomes by Use of Culture Dish (2D) as Scaffold (Comparative Example)

A Comparative Example of recovering exosomes after culturing by the use of a culture dish (2D) as a scaffold and further culturing with the amount of sugar consumed being a plateau will be described below.

BMSCs and ADSCs were seeded on the scaffold. The scaffold used was a 6 cm cell-culture dish (2D, adherent cell-culture dish, manufactured by Sumitomo Bakelite Co., Ltd.). To each of the wells, $6 \times 10^3$ cells were seeded for BMSCs, and $4 \times 10^4$ cells were seeded for ADSCs. A basal medium was 1.5 ml of 10% FBS/DMEM F12 (Sigma-Aldrich).

Starting from Day 2, 1.5 ml of medium was exchanged daily, and the amount of sugar consumed in the used culture medium was measured. The culturing was continued until the amount of sugar consumed by the cells reached a plateau. The culture time until the amount of sugar consumed reached a plateau was 10 days for BMSCs. The culture time until the amount of sugar consumed reached a plateau was 8 days for ADSCs.

Subsequently, the medium was exchanged immediately after the amount of sugar consumed by BMSCs and ADSCs began to a plateau. A medium used was the one obtained by adding 10% ExoFBS (Funakoshi Co., Ltd.) to DMEM F12. BMSCs and ADSCs were cultured for 48 hours after the exchange of the medium.

The total of 1.5 ml of conditioned medium was collected after the culturing of BMSCs and ADSCs for 48 hours. Exosomes were then recovered from the collected conditioned medium.

3. Recovery of Exosomes after Culturing and Before Plateau of Amount of Sugar Consumed A Comparative Example of recovering exosomes after culturing and before the plateau of the amount of sugar consumed will be described below.

BMSCs and ADSCs were seeded on a scaffold. The scaffold used was a nonwoven fabric (3D, BioNOCII, manufactured by CESCO, in a non-adherent 24 well plate (PrimeSurface (registered trademark) manufactured by Sumitomo Bakelite Co., Ltd.) having a three-dimensional structure and a 6 cm cell-culture dish (2D, adherent cell-culture dish, manufactured by Sumitomo Bakelite Co., Ltd.). To each of the wells of the nonwoven fabric scaffold and the culture dish scaffold, $6 \times 10^3$ cells were seeded for BMSCs, and $4 \times 10^4$ cells were seeded for ADSCs. A basal medium was 1.5 ml of 10% FBS/DMEM F12 (Sigma-Aldrich).

Starting from Day 2, 1.5 ml of medium was exchanged daily, and the amount of sugar consumed in the used culture medium was measured. The culturing of BMSCs and ADSCs was continued on the nonwoven fabric scaffold and the culture dish scaffold until Day 7 which is before the plateau of the amount of sugar consumed by the cells.

Then, the medium was exchanged immediately after Day 7. A medium used was the one obtained by adding 10% ExoFBS (Funakoshi Co., Ltd.) to DMEM F12. After the exchange of the medium, BMSCs and ADSCs were further cultured on the nonwoven fabric scaffold and in the culture dish scaffold for 48 hours. The total of 1.5 ml of conditioned medium was collected after the culturing for 48 hours. Exosomes were then recovered from the collected conditioned medium.

4. Evaluation of Exosomes 4-1. Effect of Using Nonwoven Fabric Having Three-Dimensional Structure Of 1.5 ml of the conditioned medium collected in total, 50 µl per an evaluation item was subjected to measurement with ExoCounter (JVCKENWOOD) (CD63 and CD81 were quantitatively determined as exosome markers).

FIG. 1 shows a relationship between the amount of sugar consumed and the culture time in culturing of BMSCs by the use of a nonwoven fabric as a scaffold. As illustrated in FIG. 1, y=5.4833x+4.287 was determined as an approximate line from plotted values, and the amount of sugar consumed was confirmed to reach a plateau on Day 10.

Figure 2:
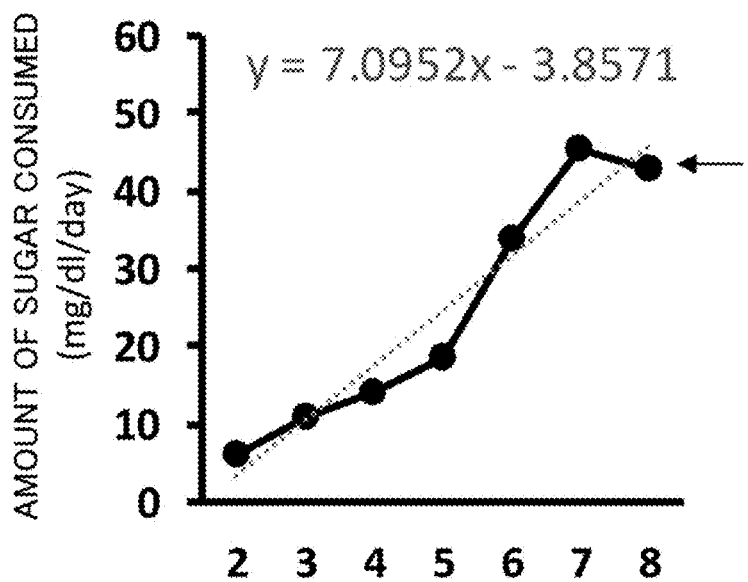
FIG. 2 is a graph showing a relationship between the amount of sugar consumed and a culture time in culturing of adipose-derived mesenchymal stem cells by using a nonwoven fabric as a scaffold.

FIG. 2 shows a relationship between the amount of sugar consumed and the culture time in culturing of ADSCs by the use of a nonwoven fabric as a scaffold. As illustrated in FIG. 2, y=7.0952x−3.8571 was determined as an approximate line from plotted values, and the amount of sugar consumed was confirmed to reach a plateau on Day 8.

Next, the amounts of exosomes yielded compensated by the final cell counts on the respective scaffolds for each cells were compared and considered.

The following Table 1 shows the cell counts of BMSCs and ADSCs.

TABLE 1

| Cell Strain | Scaffold | Cell Count (×10$^5$) | Viability (%) | 3D/2D ratio |
|---|---|---|---|---|
| BMSC | 2D | 2.24 ± 0.13 | 99.0 ± 0.23 | ×1.18 |
|  | 3D | 2.64 ± 0.07 | 97.5 ± 0.49 |  |
| ADSC | 2D | 2.18 ± 0.11 | 99.0 ± 0.26 | ×0.78 |
|  | 3D | 1.69 ± 0.07 | 98.2 ± 0.22 |  |

Figure 3:
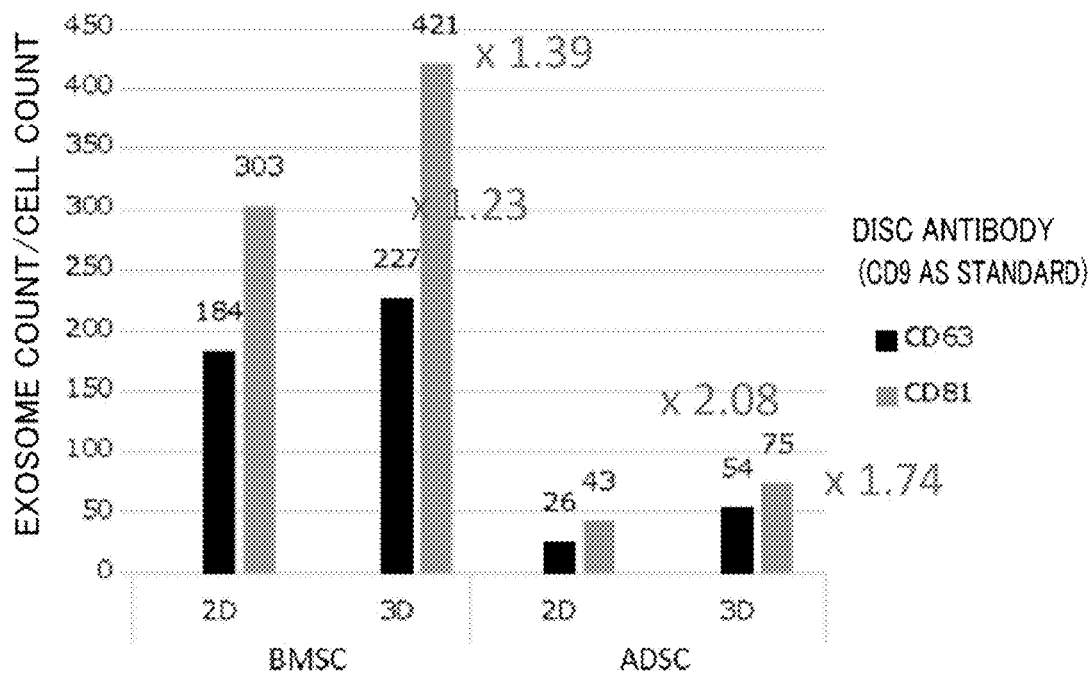
FIG. 3 is a graph showing a comparison in the number of exosomes compensated by a final cell count between culturing on a nonwoven fabric (3D) and culturing in a culture dish (2D) for bone marrow-derived mesenchymal stem cells and adipose-derived mesenchymal stem cells.

Each numerical value of the number of exosomes measured with ExoCounter was compensated by the final cell count of each specimen (FIG. 3). The number of exosomes as CD63 per the number of BMSCs was ×1.23 times larger in the culturing on the 3D nonwoven fabric than in the culturing in the 2D culture dish. The number of exosomes as CD81 per the number of BMSCs was ×1.39 times larger in the culturing on the 3D nonwoven fabric than in the culturing on the 2D culture dish. The number of exosomes as CD63 per the number of ADSCs was ×2.08 larger in the culturing on the 3D nonwoven fabric than in the culturing in the 2D culture dish. The number of exosomes as CD81 per the number of ADSCs was ×1.74 larger in the culturing on the 3D nonwoven fabric than in the culturing in the 2D culture dish.

As can be seen from the above, for both of BMSCs and ADSCs, the increase in the amount of exosomes yielded by the exosome recovery method using the culturing on nonwoven fabric (3D) was demonstrated.

Figure 4:
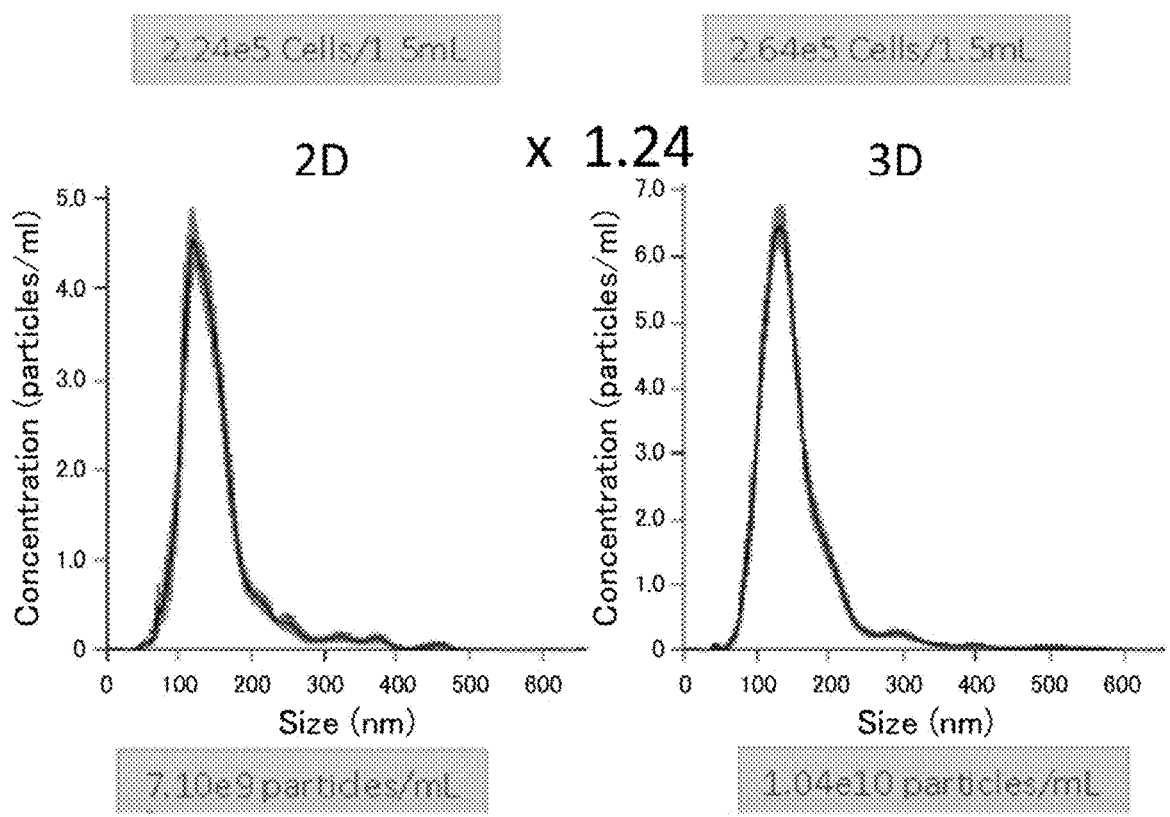
FIG. 4 shows graphs showing a comparison in the number of exosomes obtained by NTA measurement between culturing on a nonwoven fabric (3D) and culturing in a culture dish (2D) for bone marrow-derived mesenchymal stem cells.

For BMSCs, NTA-measurements (particle distribution, a compensation value of cell count ratio (3D/2D ratio)) were performed, and results thereof were compared and considered. From the values (3D: 10.1×10$^9$ cells, 2D: 7.1×10$^9$ cells) obtained by the NTA measurements, the 3D/2D ratio was ×1.46, and the increase rate of the amount of exosomes compensated by the cell count ratio (×1.18) in Table 1 was ×1.24 (FIG. 4). As can be seen from the above, the increase in the amount of exosomes yielded was demonstrated through the NTA measurements.

4-2. Effect of Culturing Until Amount of Sugar Consumed Reaches Plateau

When the culturing of BMSCs and ADSCs was continued on the nonwoven fabric scaffold (3D) and in the culture dish scaffold (2D) until Day 7 which is before the plateau of the amount of sugar consumed by the cells, the cell count for the nonwoven fabric scaffold was 1.11±0.04×10$^5$, and that for the culture dish scaffold was 1.43±0.12×10$^5$. The cell count for the nonwoven fabric scaffold (3D)/the cell count for the culture dish scaffold (2D) ratio=×0.776.

The amounts of exosomes as CD63 yielded were 145,863 on the nonwoven fabric scaffold (3D) and 189,653 in the culture dish scaffold (2D). The 3D/2D ratio of the amount of exosomes as CD63 yielded on 3D/the amount of exosomes as CD63 yielded in 2D=×0.769. The numerical value obtained by compensating, with the cell count ratio, the ratio of the amount of exosomes yielded was 0.99, which demonstrated that the use of the nonwoven fabric scaffold (3D) does not cause the amount of exosomes yielded to increase.

The amounts of exosomes as CD81 yielded were 139,287 on the nonwoven fabric scaffold (3D) and 186,584 in the culture dish scaffold (2D). The 3D/2D ratio of the amount of exosomes as CD81 yielded on 3D/the amount of exosomes as CD81 yielded in 2D=×0.747. The numerical value obtained by compensating, with the cell count ratio, the ratio of the amount of exosomes yielded was 0.96, which demonstrated that the use of the nonwoven fabric scaffold (3D) does not cause the amount of exosomes yielded to increase.

As can be seen from the above, mere use of the nonwoven fabric (3D) for both BMSC and ADSC does not cause the amount of exosomes yielded to increase, but (a) culturing by the use of nonwoven fabric (3D) as a scaffold and (b) further culturing with the amount of sugar consumed being a plateau cause the amount of exosomes yielded to increase.

The invention claimed is:

1. A method of increasing an amount of exosomes yielded from mesenchymal stem cells, the method comprising:
   a three-dimensional culture step of three dimensionally culturing mesenchymal stem cells in a medium by using a nonwoven fabric as a scaffold while measuring an amount of substance metabolized by the mesenchymal stem cells which is in the medium;
   a post-plateau culture step of further: (i) culturing for a certain period of time after the amount of the substance in the medium reaches a plateau and (ii) increasing the amount of exosomes yielded from the mesenchymal stem cells; and
   an exosome recovery step of recovering exosomes including CD63 and CD81 from the mesenchymal stem cells after the culturing for the certain period of time; wherein the substance metabolized by the mesenchymal stem cells which is in the medium is sugar.

2. The method of claim 1, wherein:
   an amount of the sugar consumed by the mesenchymal stem cells relative to a culture time is measured, and
   the post-plateau culture step includes further culturing for a certain period of time after the amount of the sugar consumed reaches a plateau.

3. The method of claim 2, wherein, in the post-plateau culture step, the measuring the amount of the sugar consumed by the mesenchymal stem cells relative to the culture time includes measuring an amount of glucose consumed.

4. The method of claim 1, wherein, in the post-plateau culture step, a culture time after the amount of the substance reaches a plateau is 24 hours or more to 72 hours or less.

5. The method of claim 1, wherein the mesenchymal stem cells are adipose-derived mesenchymal stem cells.

6. The method of claim 1, wherein, when the mesenchymal stem cells are adipose-derived mesenchymal stem cells, a culture time for the adipose-derived mesenchymal stem cells in the three dimensional culture step is 7 days or more to 9 days or less.

7. The method of claim 1, wherein the mesenchymal stem cells are bone marrow-derived mesenchymal stem cells.

8. The method of claim 1, wherein, when the mesenchymal stem cells are bone marrow-derived mesenchymal stem cells, a culture time for the bone marrow-derived mesenchymal stem cells in the three dimensional culture step is 9 days or more to 11 days or less.

* * * * *

UNITED STATES PATENT AND TRADEMARK OFFICE
CERTIFICATE OF CORRECTION

| | |
|---|---|
| PATENT NO. | : 11,613,734 B2 |
| APPLICATION NO. | : 17/619128 |
| DATED | : March 28, 2023 |
| INVENTOR(S) | : Chiba |

It is certified that error appears in the above-identified patent and that said Letters Patent is hereby corrected as shown below:

In the Claims

Column 10,
Lines 26 & 39, "fora" should read --for a--.

Signed and Sealed this
Eighth Day of August, 2023

Katherine Kelly Vidal
*Director of the United States Patent and Trademark Office*